(12) United States Patent
Al-Ali

(10) Patent No.: US 7,027,849 B2
(45) Date of Patent: Apr. 11, 2006

(54) BLOOD PARAMETER MEASUREMENT SYSTEM

(75) Inventor: Ammar Al-Ali, Tustin, CA (US)

(73) Assignee: Masimo Laboratories, Inc., Irvine, CA (US)

( * ) Notice: Subject to any disclaimer, the term of this patent is extended or adjusted under 35 U.S.C. 154(b) by 5 days.

(21) Appl. No.: 10/719,928

(22) Filed: Nov. 21, 2003

(65) Prior Publication Data

US 2004/0107065 A1    Jun. 3, 2004

Related U.S. Application Data

(60) Provisional application No. 60/428,419, filed on Nov. 22, 2002.

(51) Int. Cl.
*A61B 5/00* (2006.01)

(52) U.S. Cl. .................................... 600/323; 702/104

(58) Field of Classification Search ............. 702/104, 702/127, 134, 135; 356/39–42; 600/332–342
See application file for complete search history.

(56) References Cited

U.S. PATENT DOCUMENTS

| | | | |
|---|---|---|---|
| 4,854,699 A * | 8/1989 | Edgar, Jr. .................. | 356/41 |
| 4,890,619 A * | 1/1990 | Hatschek ................... | 600/323 |
| 5,337,744 A | 8/1994 | Branigan | |
| 5,452,717 A | 9/1995 | Branigan et al. | |
| 5,482,036 A | 1/1996 | Diab et al. | |
| 5,490,505 A | 2/1996 | Diab et al. | |
| 5,490,506 A * | 2/1996 | Takatani et al. ........... | 600/309 |
| 5,564,108 A | 10/1996 | Hunsaker et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,823,950 A | 10/1998 | Diab et al. | |
| 5,827,182 A * | 10/1998 | Raley et al. ................ | 600/323 |
| 5,860,919 A | 1/1999 | Kiani-Azarbayjany et al. | |
| 5,890,929 A | 4/1999 | Mills et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |

(Continued)

FOREIGN PATENT DOCUMENTS

WO    WO 00/42911 A1    7/2000

*Primary Examiner*—Michael Nghiem
*Assistant Examiner*—Demetrius Pretlow
(74) *Attorney, Agent, or Firm*—Knobbe, Martens, Olson & Bear, LLP

(57) ABSTRACT

A blood parameter measurement system has a monitor configured to provide an oxygen saturation measurement based upon the absorption of two wavelengths of optical radiation by a tissue site. A software upgrade is installable in the monitor so as to enable the monitor to operate in conjunction with a multiple wavelength sensor. A wavelength controller is adapted to the upgrade so as to drive the sensor.

19 Claims, 16 Drawing Sheets

U.S. PATENT DOCUMENTS

| | | | |
|---|---|---|---|
| 6,023,541 A | 2/2000 | Merchant et al. | |
| 6,036,642 A | 3/2000 | Diab et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,334,065 B1 | 12/2001 | Al-Ali et al. | |
| 6,349,228 B1 | 2/2002 | Kiani et al. | |
| 6,360,113 B1 * | 3/2002 | Dettling | 600/322 |
| 6,360,114 B1 | 3/2002 | Diab et al. | |
| 6,371,921 B1 | 4/2002 | Caro et al. | |
| 6,377,829 B1 | 4/2002 | Al-Ali | |
| 6,388,240 B1 | 5/2002 | Schulz et al. | |
| 6,397,091 B1 | 5/2002 | Diab et al. | |
| 6,430,525 B1 | 8/2002 | Weber et al. | |
| 6,463,311 B1 | 10/2002 | Diab | |
| 6,470,199 B1 * | 10/2002 | Kopotic et al. | 600/344 |
| 6,501,975 B1 | 12/2002 | Diab et al. | |
| 6,515,273 B1 | 2/2003 | Al-Ali | |
| 6,525,386 B1 | 2/2003 | Mills et al. | |
| 6,526,300 B1 | 2/2003 | Kiani et al. | |
| 6,541,756 B1 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 * | 6/2003 | Ali et al. | 600/323 |
| 6,597,933 B1 | 7/2003 | Kiani et al. | |
| 6,606,511 B1 | 8/2003 | Ali et al. | |
| 6,632,181 B1 | 10/2003 | Flaherty et al. | |
| 6,640,116 B1 | 10/2003 | Diab | |
| 6,643,530 B1 | 11/2003 | Diab et al. | |
| 6,650,917 B1 | 11/2003 | Diab et al. | |
| 6,654,624 B1 | 11/2003 | Diab et al. | |
| 6,658,276 B1 * | 12/2003 | Kianl et al. | 600/322 |
| 6,671,531 B1 | 12/2003 | Al-Ali et al. | |
| 6,678,543 B1 | 1/2004 | Diab et al. | |
| 6,684,090 B1 | 1/2004 | Ali et al. | |
| 6,694,157 B1 * | 2/2004 | Stone et al. | 600/310 |
| 6,697,656 B1 | 2/2004 | Al-Ali | |
| 6,697,658 B1 | 2/2004 | Al-Ali | |
| RE38,476 E | 3/2004 | Diab et al. | |
| 6,699,194 B1 | 3/2004 | Diab et al. | |
| 6,714,804 B1 | 3/2004 | Al-Ali et al. | |
| RE38,492 E | 4/2004 | Diab et al. | |
| 6,725,075 B1 | 4/2004 | Al-Ali | |
| 6,770,028 B1 * | 8/2004 | Ali et al. | 600/300 |
| 2001/0029326 A1 * | 10/2001 | Diab et al. | 600/364 |
| 2002/0013518 A1 | 1/2002 | West et al. | |
| 2002/0038081 A1 | 3/2002 | Fein et al. | |
| 2002/0173706 A1 * | 11/2002 | Takatani | 600/323 |

* cited by examiner

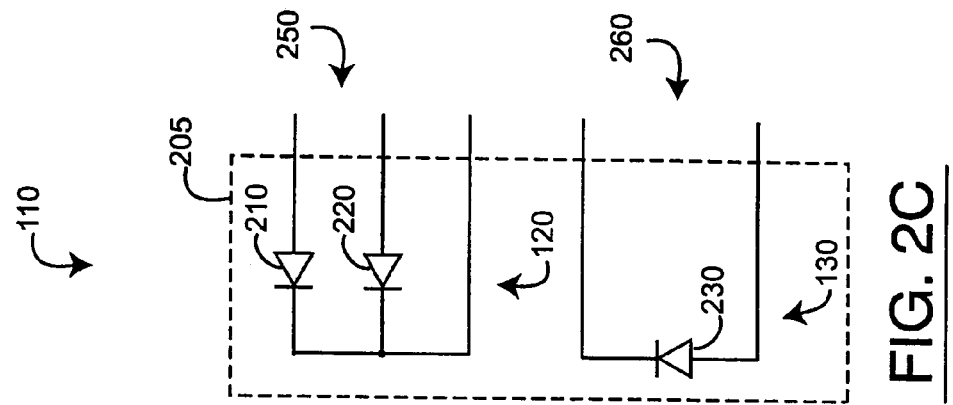
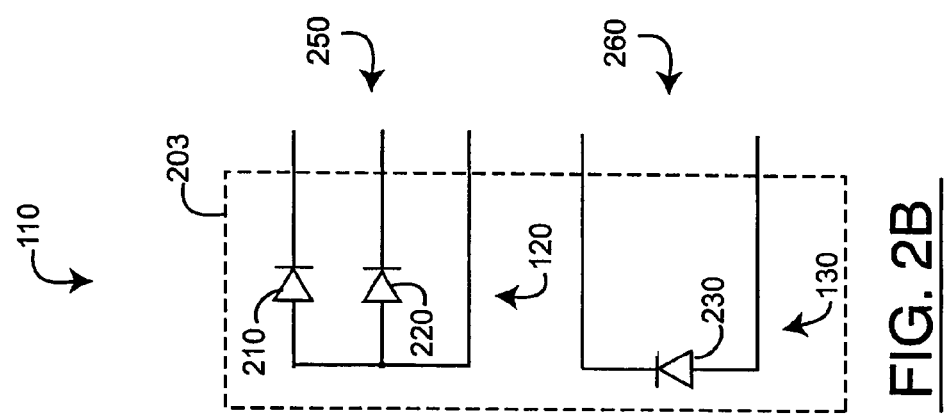
(Prior Art)
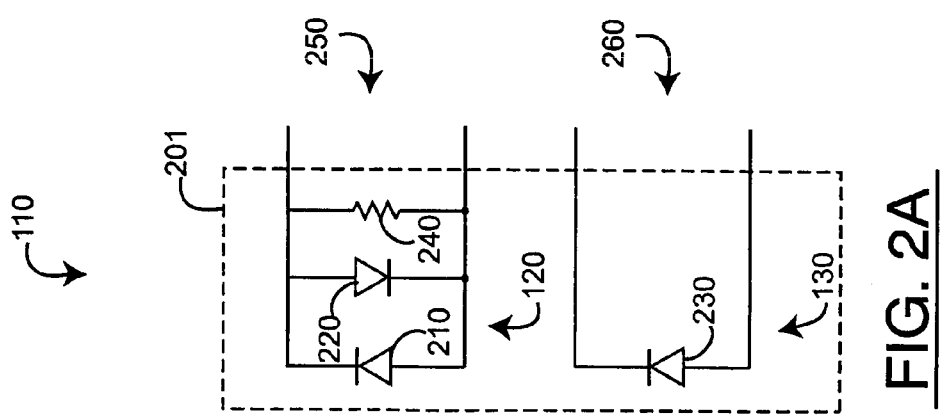

US 7,027,849 B2

BLOOD PARAMETER MEASUREMENT SYSTEM

CROSS-REFERENCE TO RELATED APPLICATION

The present application claims priority benefit under 35 U.S.C. §119(e) from U.S. Provisional Application No. 60/428,419, filed Nov. 22, 2002 entitled "Blood Parameter Measurement System," which is incorporated herein by reference.

BACKGROUND OF THE INVENTION

Pulse oximetry is a noninvasive, easy to use, inexpensive procedure for measuring the oxygen saturation level of arterial blood. Pulse oximeters perform a spectral analysis of the pulsatile component of arterial blood in order to determine the relative concentration of oxygenated hemoglobin, the major oxygen carrying constituent of blood. By providing early detection of decreases in the arterial oxygen supply, pulse oximetry reduces the risk of accidental death and injury. As a result, pulse oximeters have gained rapid acceptance in a wide variety of medical applications, including surgical wards, intensive care units, general wards and home care.

FIG. 1 illustrates a pulse oximetry system 100 having a sensor 110 and a monitor 140. The sensor 110 has emitters 120 and a detector 130 and is attached to a patient at a selected tissue site, such as a fingertip or ear lobe. The emitters 120 project light through the blood vessels and capillaries of the tissue site. The detector 130 is positioned so as to detect the emitted light as it emerges from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

Also shown in FIG. 1, the monitor 140 has drivers 150, a controller 160, a front-end 170, a signal processor 180, a display 190. The drivers 150 alternately activate the emitters 120 as determined by the controller 160. The front-end 170 conditions and digitizes the resulting current generated by the detector 130, which is proportional to the intensity of the detected light. The signal processor 180 inputs the conditioned detector signal and determines oxygen saturation, as described below, along with pulse rate. The display 190 provides a numerical readout of a patient's oxygen saturation and pulse rate. A pulse oximetry monitor is described in U.S. Pat. No. 5,482,036 entitled "Signal Processing Apparatus and Method," which is assigned to Masimo Corporation, Irvine, Calif. and incorporated by reference herein.

FIGS. 2A–C illustrate various circuits 201–205 for a pulse oximetry sensor 110. A typical sensor 110 has emitters 120 including both red and infrared LEDs 210, 220 and a detector 130 consisting of a photodiode 230. LED pinouts 250 connect the LEDs 210, 220 to the drivers 150 (FIG. 1) via a patient cable (not shown). Detector pinouts 260 connect the photodiode 230 to the front-end 170 (FIG. 1) also via the patient cable. FIG. 2A illustrates a back-to-back sensor circuit 201, where the LEDs 210, 220 are connected in parallel such that the anode of one LED 210 is connected to the cathode of the other LED 220 and vice-a-versa. The sensor circuit 201 may have an information element 240, such as a resistor. The information element 240 has multiple uses depending on the manufacturer, such as an indicator sensor type. An information element is described in U.S. Pat. No. 5,758,644 entitled "Manual and Automatic Probe Calibration," which is assigned to Masimo Corporation, Irvine, Calif. and incorporated by reference herein. FIGS. 2B–C illustrate alternative sensor circuits. FIG. 2B illustrates a common anode sensor circuit 203 having LEDs 210, 220 with connected anodes provided as a common one of the pinouts 250. FIG. 2C illustrates a common cathode sensor circuit 205 having LEDs 210, 220 with connected cathodes provided as a common one of the pinouts 250.

FIGS. 3A–C illustrate drive signal timing corresponding to the sensor circuits described with respect to FIGS. 2A–C, above. FIG. 3A is a timing diagram 300 of the drive signal 152 (FIG. 1) illustrating the relative occurrence and duration of control waveforms transmitted from the drivers 150 (FIG. 1) to the emitters 120 (FIG. 1). A typical drive signal 152 (FIG. 1) has a red LED enable period 310, an IR LED enable period 330 and a dark period 320 between the enable periods 310, 330. During an enable time period 310, 330, drive current is supplied from the drivers 150 (FIG. 1) to one of the LED emitters 210, 220 (FIGS. 2A–C), causing the selected LED to turn on and emit optical energy at a particular wavelength (red or IR), which is transmitted into a tissue site. During a dark period 320, no drive current is supplied to the LEDs 210, 220 (FIGS. 2A–C), turning both off. Red LED enable periods 310 are alternated with IR LED enable periods 330 so that concurrent tissue site responses at both red and IR wavelengths can be measured. The timing diagram 300 illustrates a typical 25% "on" duty cycle for a particular LED. The dark periods 320 allow the signal processor 180 (FIG. 1) to demodulate or separate the red wavelength response from the IR wavelength response. Detector signal demodulation is described in U.S. Pat. No. 5,919,134 entitled "Method and Apparatus for Demodulating Signals in a Pulse Oximetry System," which is assigned to Masimo Corporation, Irvine, Calif. and incorporated by reference herein.

FIG. 3B is a graph 302 of drive current versus time for a back-to-back sensor circuit 201 (FIG. 2A), corresponding to the timing diagram 300 (FIG. 3A), described above. During the red LED enable periods 310 (FIG. 3A), the drive signal 152 (FIG. 1) has a first polarity drive current 312 of a first amplitude, so that the red LED emits at a predetermined intensity. During the IR LED enable time periods 330 (FIG. 3A), the drive signal 152 (FIG. 1) has an second, opposite polarity drive current 332 of a second amplitude, so that the IR LED emits at a predetermined intensity. During the dark periods 320 (FIG. 3A) the drive signal 152 (FIG. 1) has no drive current 322. In this manner, the timing and intensity of the red and IR LED emissions may be independently controlled with a single drive signal 152 (FIG. 1) having bipolar drive current communicated over a single pair of conductors connected to the LED pinouts 250 (FIG. 2A).

FIG. 3C are two graphs 304, 306 of drive current versus time for a common cathode sensor circuit 205 (FIG. 2C) or, similarly, for a common anode sensor circuit 203 (FIG. 2B), corresponding to the timing diagram 300 (FIG. 3A), described above. During the red LED enable periods 310 (FIG. 3A), one drive signal 152 (FIG. 1) has a drive current 314 of a first amplitude, so that the red LED emits at a predetermined intensity. During the IR LED enable time periods 330 (FIG. 3A), another drive signal 152 (FIG. 1) has a drive current 334 of a second amplitude, so that the IR LED emits at a predetermined intensity. During the dark periods 320 (FIG. 3A) the drive signals 152 (FIG. 1) have no drive current 324, 326. In this manner, the timing and intensity of the red and IR LED emissions may be independently controlled with two drive signals 152 (FIG. 1) each having unipolar drive current communicated over three conductors, including a common conductor, connected to the LED pinouts 250 (FIG. 2C).

SUMMARY OF THE INVENTION

The Beer-Lambert law provides a simple model that describes a tissue site response to pulse oximetry measurements. The Beer-Lambert law states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\epsilon_{i,\lambda}$ at a particular wavelength $\lambda$. In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \epsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve EQS. 1-2 are the number of significant absorbers that are present in the solution. For pulse oximetry, wavelengths are chosen such that, normally, there are only two significant absorbers. These are oxygenated hemoglobin ($HbO_2$) and deoxygenated hemoglobin (Hb). Thus, pulse oximetry measurements are conventionally made at two wavelengths including a red wavelength, such as 660 nm, and an infrared wavelength, such as 940 nm.

There is a need to provide a noninvasive, easy to use, inexpensive procedure to measure multiple blood parameters, other than, or in addition to, $HbO_2$ and Hb. For example, hemoglobin species that are also significant under certain circumstances are carboxyhemoglobin (HbCO) and methemoglobin (MetHb). Other blood parameters that may be measured to provide important clinical information are blood glucose and total hematocrit (Hct), to name a few. An advantageous solution is to provide a software upgrade for conventional pulse oximetry so as to achieve multiple-wavelength capability, that is, the ability to measure tissue site response to optical radiation of three or more wavelengths. Such a software upgrade can be readily applied to current pulse oximetry system designs and to the widespread installed base of pulse oximeters and multiparameter patient monitors to increase measurement capabilities to include a range of important blood parameters in addition to, or instead of, oxygen saturation.

One aspect of a blood parameter measurement system is a monitor configured to provide an oxygen saturation measurement based upon the absorption of two wavelengths of optical radiation by a tissue site. A software upgrade is installable in the monitor so as to enable the monitor to operate in conjunction with a multiple wavelength sensor. A wavelength controller is adapted to the upgrade so as to drive the sensor.

Another aspect of a blood parameter measurement system is a multiplicity of emitters configured to transmit at least three distinct wavelengths of optical radiation into a tissue site. At least one detector is configured to receive the radiation after attenuation by the tissue site and to generate a corresponding detector signal output. A wavelength controller has a drive signal input and a sensor control output and is adapted to sequentially enable the emitters.

A further aspect of a blood parameter measurement system is a method having the steps of communicating a drive signal from a monitor to a sensor and synchronizing the sensor with the monitor. Additional steps include sequentially enabling a plurality of emitters of the sensor and communicating a sensor signal from the sensor to the monitor.

An additional aspect of a blood parameter measurement system is a multiple wavelength sensor means for illuminating a tissue site with at least three wavelengths and detecting a corresponding tissue site response. The system includes a software upgrade means for enabling a pulse oximetry monitor to drive the sensor and process a corresponding sensor signal. The system also includes a wavelength controller means for interfacing between the software upgrade means and the multiple wavelength sensor means.

BRIEF DESCRIPTION OF THE DRAWINGS

FIGS. 2A–C are schematic diagrams of prior art sensor circuits;

FIG. 6A is a block diagram of a blood parameter measurement system having a wavelength controller in an adaptive sensor;

FIG. 6B is a block diagram of a blood parameter measurement system having a wavelength controller in an adapter cable;

FIG. 6C is a block diagram of a blood parameter measurement system having a wavelength controller incorporated within an emitter component of an adaptive sensor;

DETAILED DESCRIPTION OF THE PREFERRED EMBODIMENT

Figure 3A:
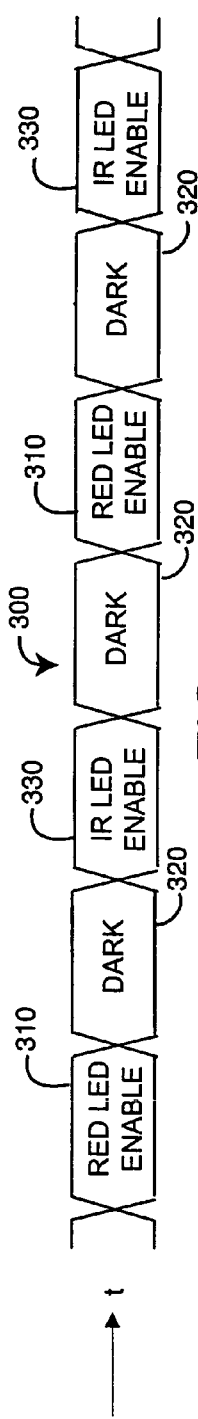
FIGS. 3A–C are a timing diagrams illustrating drive current waveforms for prior art sensor circuits.
Figure 3B:
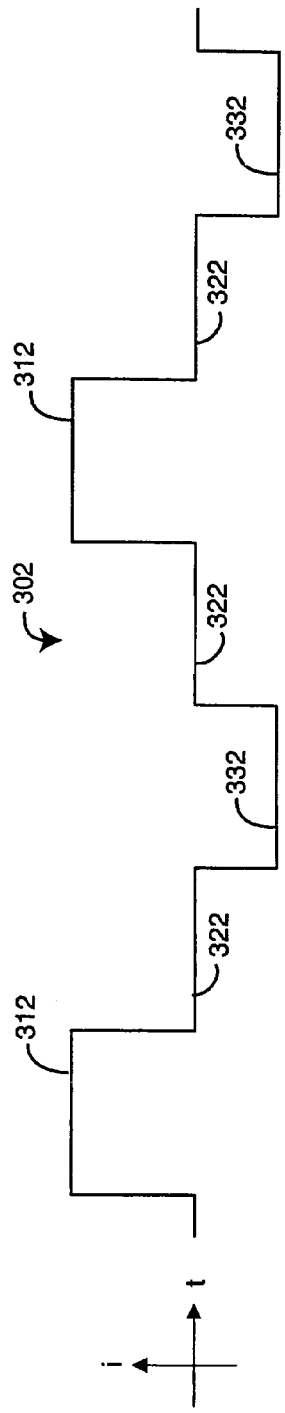
Figure 3C:
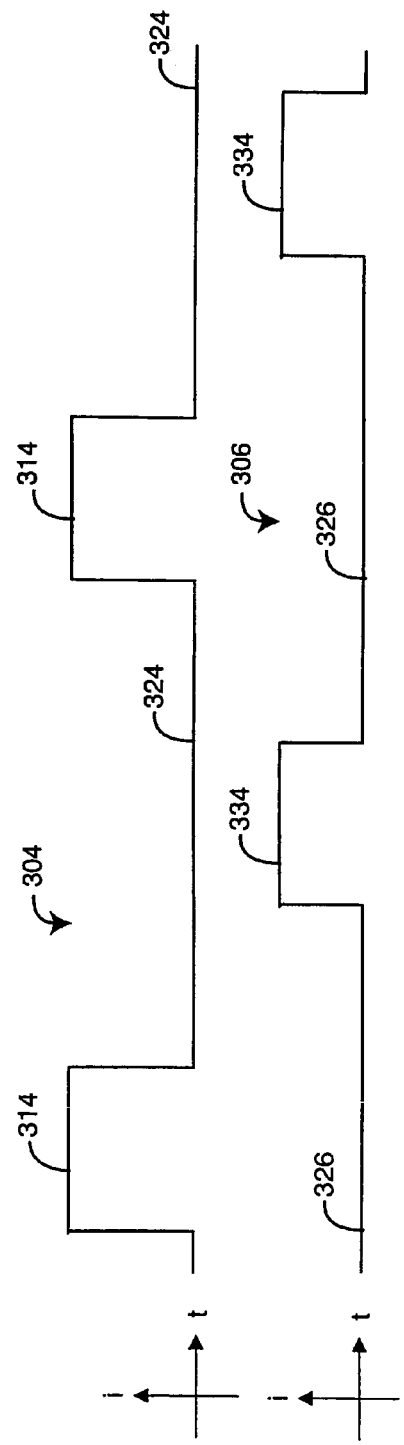
Figure 4:
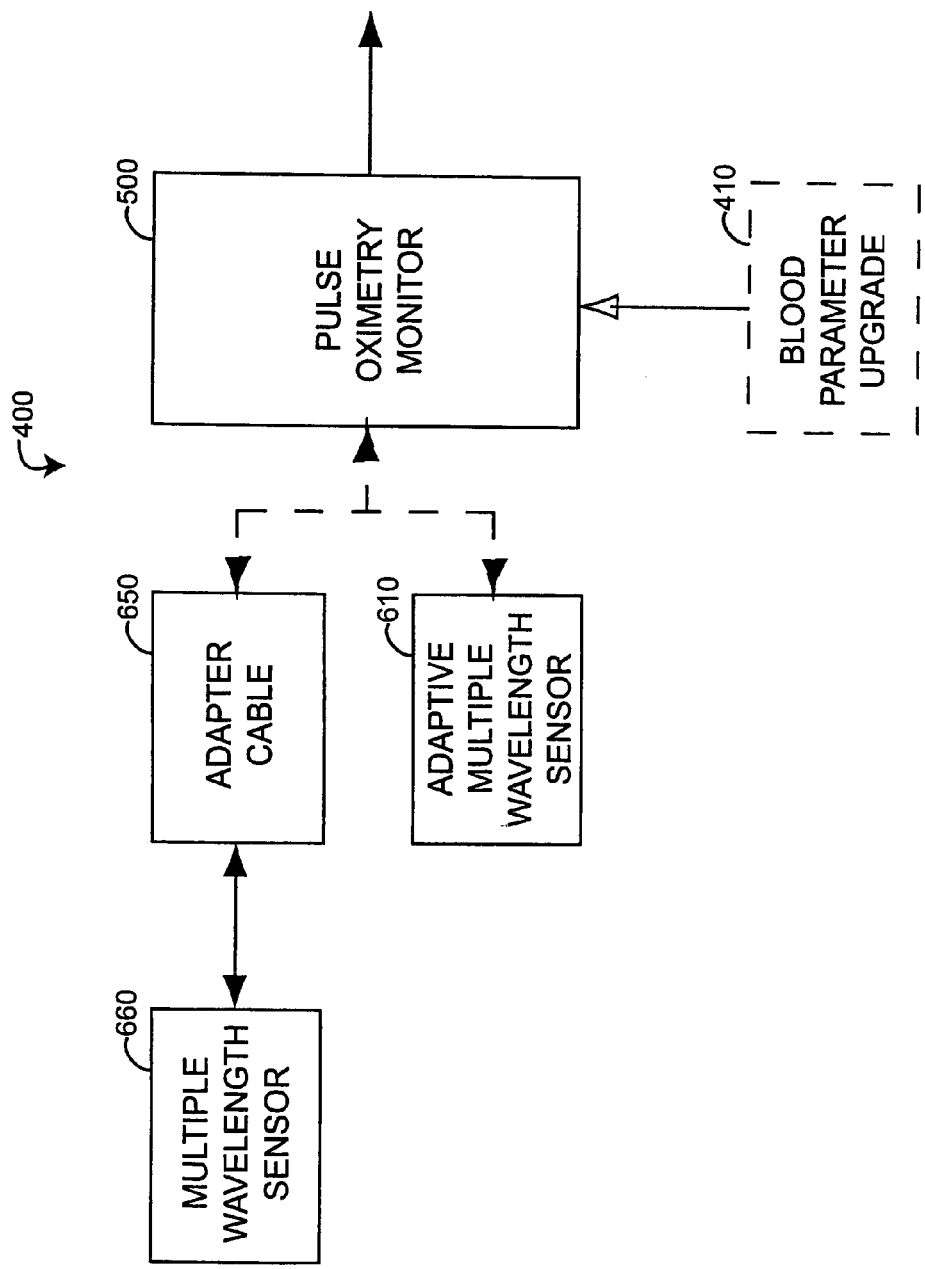
FIG. 4 is a block diagram of a blood parameter measurement system utilizing a software upgrade to a pulse oximetry monitor.

FIG. 4 illustrates a blood parameter measurement system 400 having a pulse oximetry monitor 500 and a blood parameter upgrade 410. The monitor 500 may be any pulse oximeter configured to calculate and output oxygen saturation measurements utilizing a red and IR wavelength sensor attached to a tissue site, such as described with respect to FIGS. 1–3, above. Advantageously, the monitor 500 is enabled to measure blood parameters in addition to or in lieu of oxygen saturation by a blood parameter upgrade 410 to the monitor software, without the necessity of a monitor hardware modification. In particular, the upgrade 410 enables the monitor 500 to drive a multiple wavelength sensor and to process the corresponding sensor output.

As shown in FIG. 4, the blood parameter measurement system 400 also has an adaptive multiple wavelength sensor 610 or an adapter cable 650 as alternative sensor port connections to the upgraded monitor 500. The adaptive sensor 610 is plug compatible with the monitor and functionally compatible with the blood parameter upgrade so as to provide multiple wavelength capability to the measurement system 400. The adapter cable 650 is also plug compatible with the monitor and functionally compatible with the blood parameter upgrade, but is configured to interface to an otherwise monitor incompatible multiple wavelength sensor. The blood parameter upgrade 410 is described in further detail with respect to FIG. 5, below. The adaptive sensor 610 and the adapter cable 650 are described in further detail with respect to FIGS. 6A–C, below.

Figure 1:
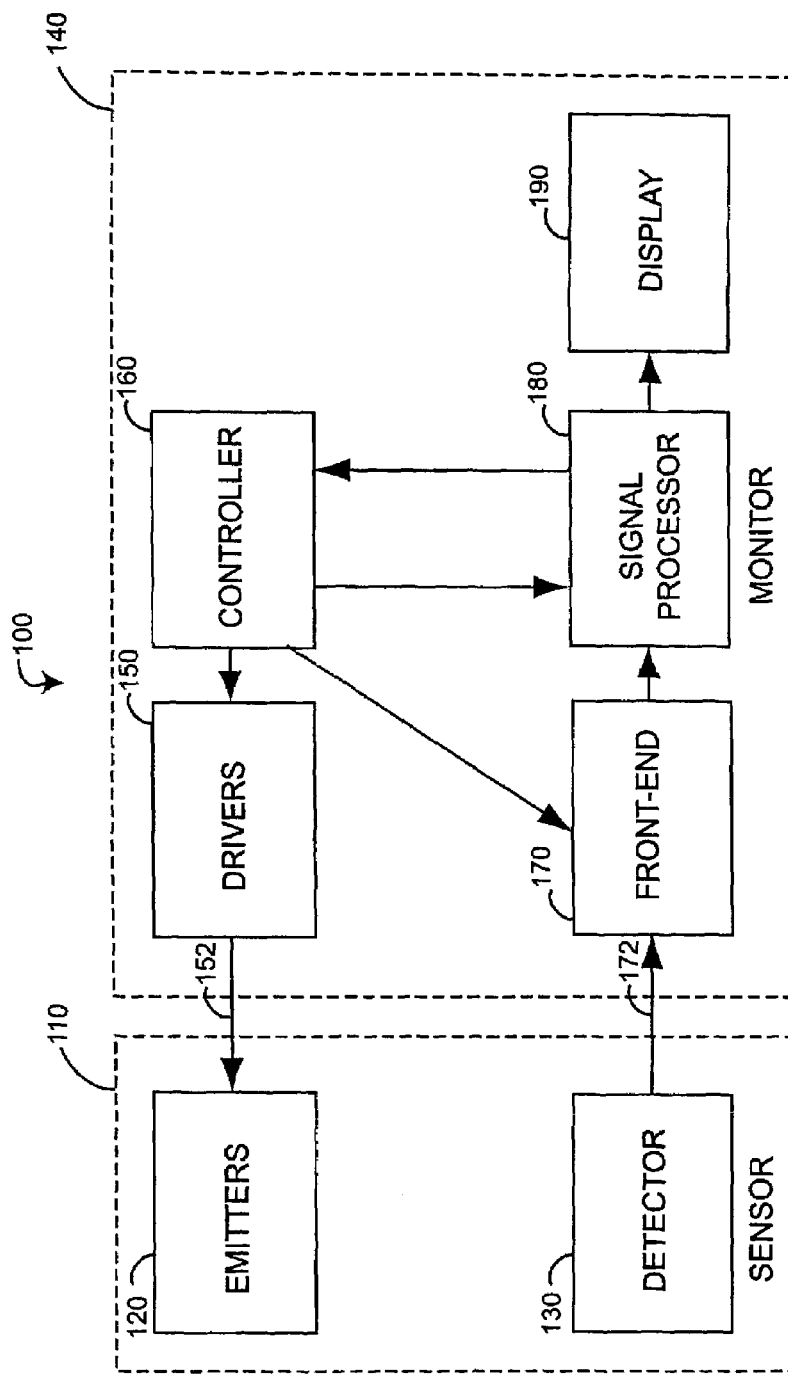
FIG. 1 is block diagram of a prior art pulse oximetry system.
Figure 5:
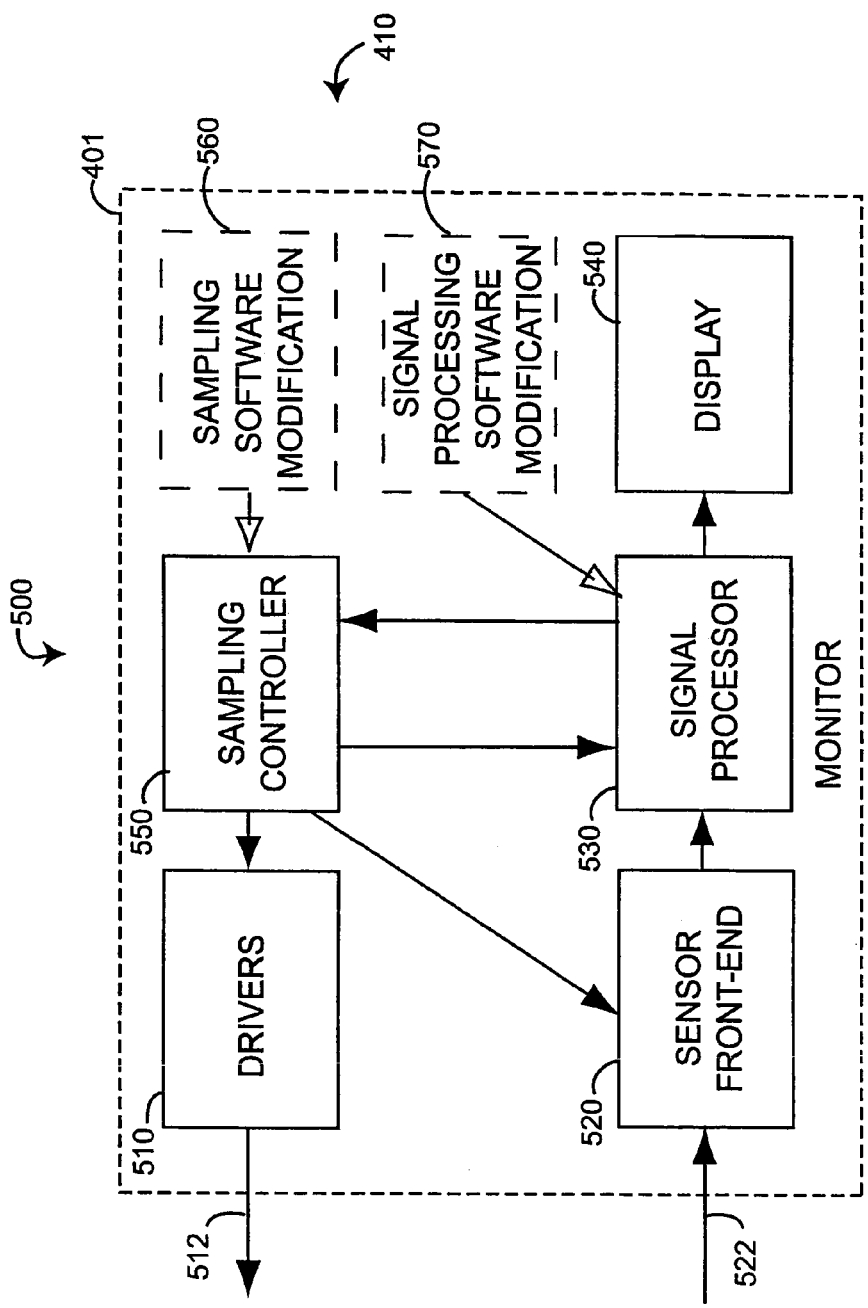
FIG. 5 is a block diagram of a monitor incorporating a blood parameter software upgrade.

FIG. 5 illustrates one embodiment of an upgraded pulse oximetry monitor 500. The monitor 500 has drivers 510, a sensor front-end 520, a signal processor 530, a display 540 and a sampling controller 550, all configured for a conventional pulse oximetry sensor 110 (FIG. 1). In particular, a drive signal 512 is physically and electrically configured to drive a red and an IR sensor emitter 120 (FIG. 1), and the sensor front-end 520 is physically and electrically configured to receive a sensor signal 522 from a detector 130 (FIG. 1).

As shown in FIG. 5, the monitor 500 has software that is upgraded to drive and process signals from a multiple wavelength sensor 610, 660 (FIG. 4) either directly or through an adapter cable 650 (FIG. 4). In one embodiment, a sampling software modification 560 enables the sampling controller 550 to encode the drive signal 512 to provide multiple wavelength control, as described below. A signal processing software modification 570 enables the signal processor 530 to demodulate a multiple wavelength detector signal 522 and to derive blood parameters from a tissue site accordingly. The sampling software modification 560 is described in detail with respect to FIGS. 6–11, below. In one embodiment, the signal processing software modification 570 implements a multiple wavelength demodulation function, such as described in U.S. Pat. No. 6,229,856 entitled "Method and Apparatus for Demodulating Signals in a Pulse Oximetry System," assigned to Masimo Corporation, Irvine, Calif. and incorporated by reference herein.

Figure 6A:
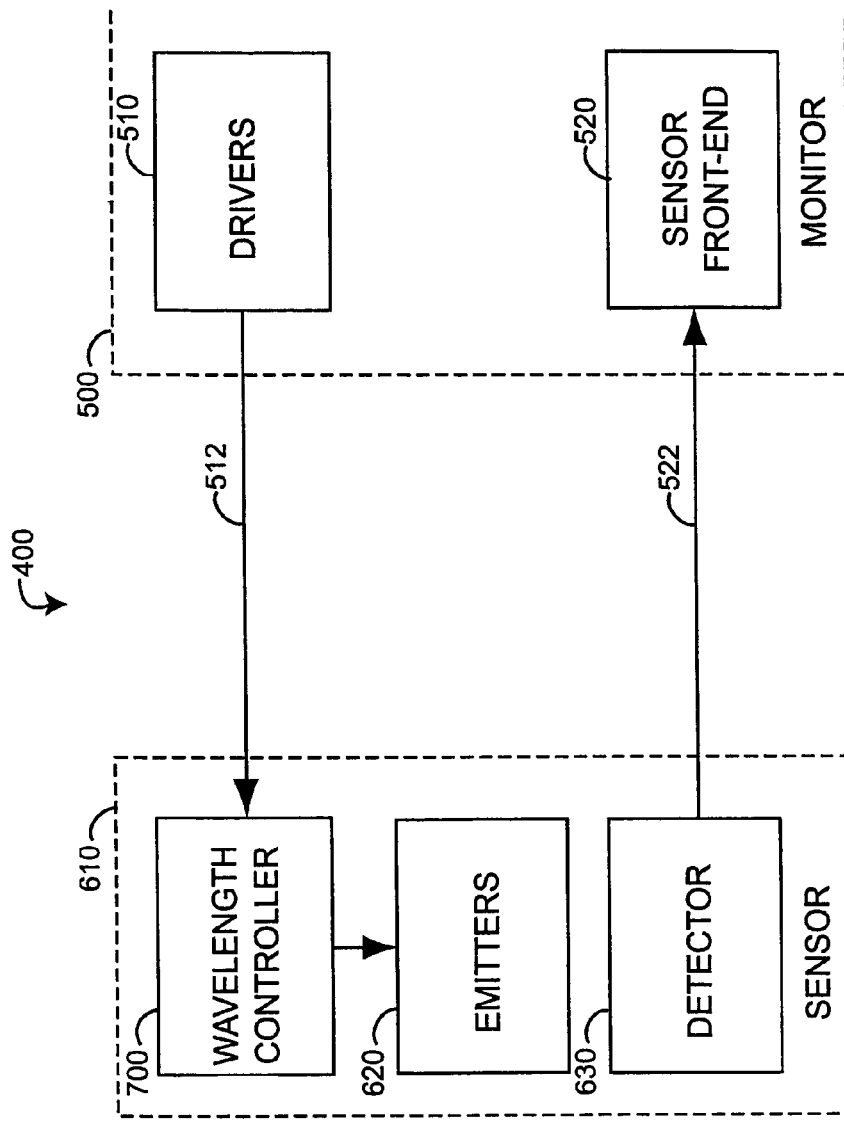
FIGS. 6A–C are block diagrams of wavelength controller configurations for interfacing a multiple wavelength sensor to an upgraded monitor.
Figure 6B:
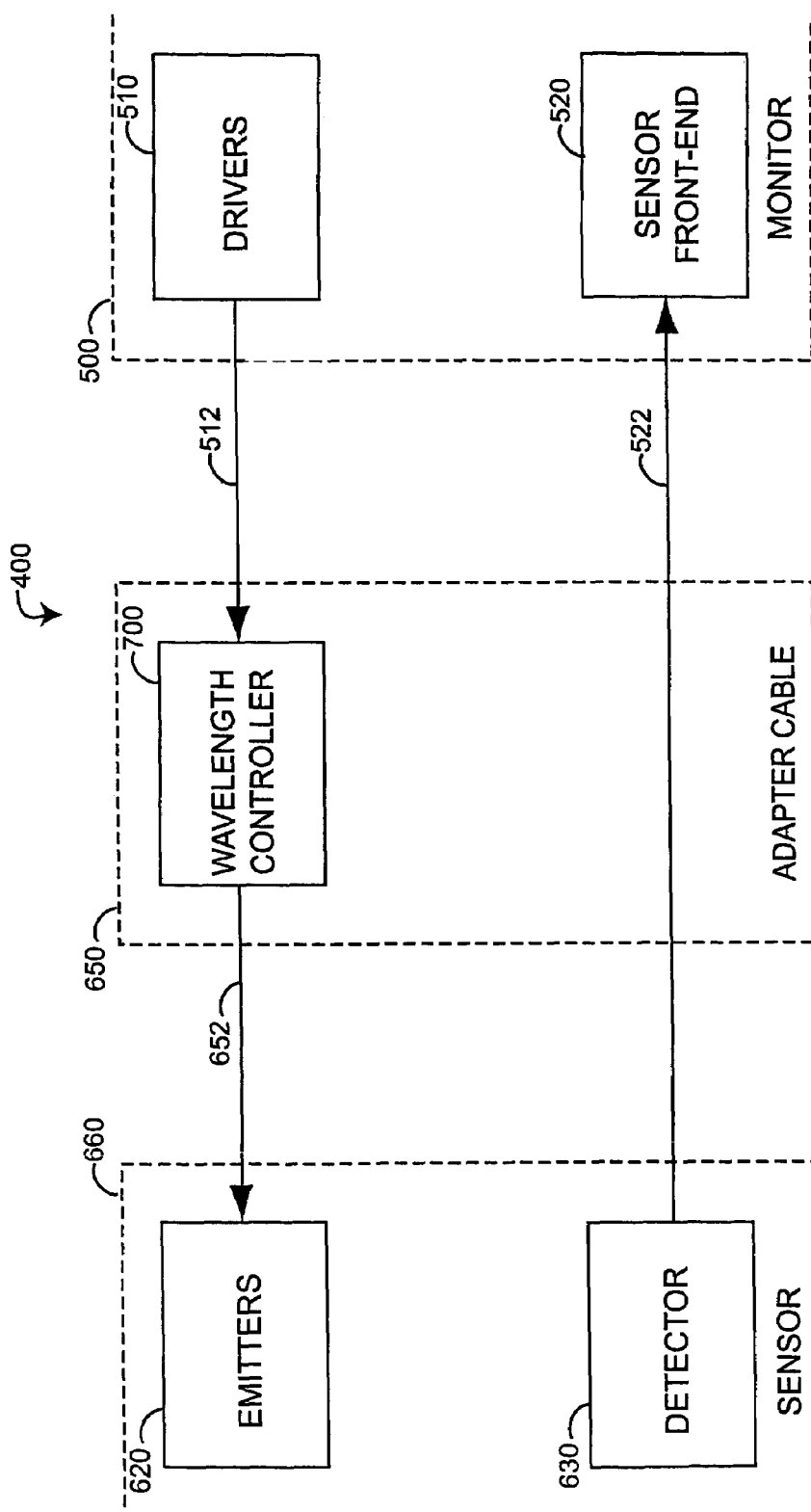
Figure 6C:
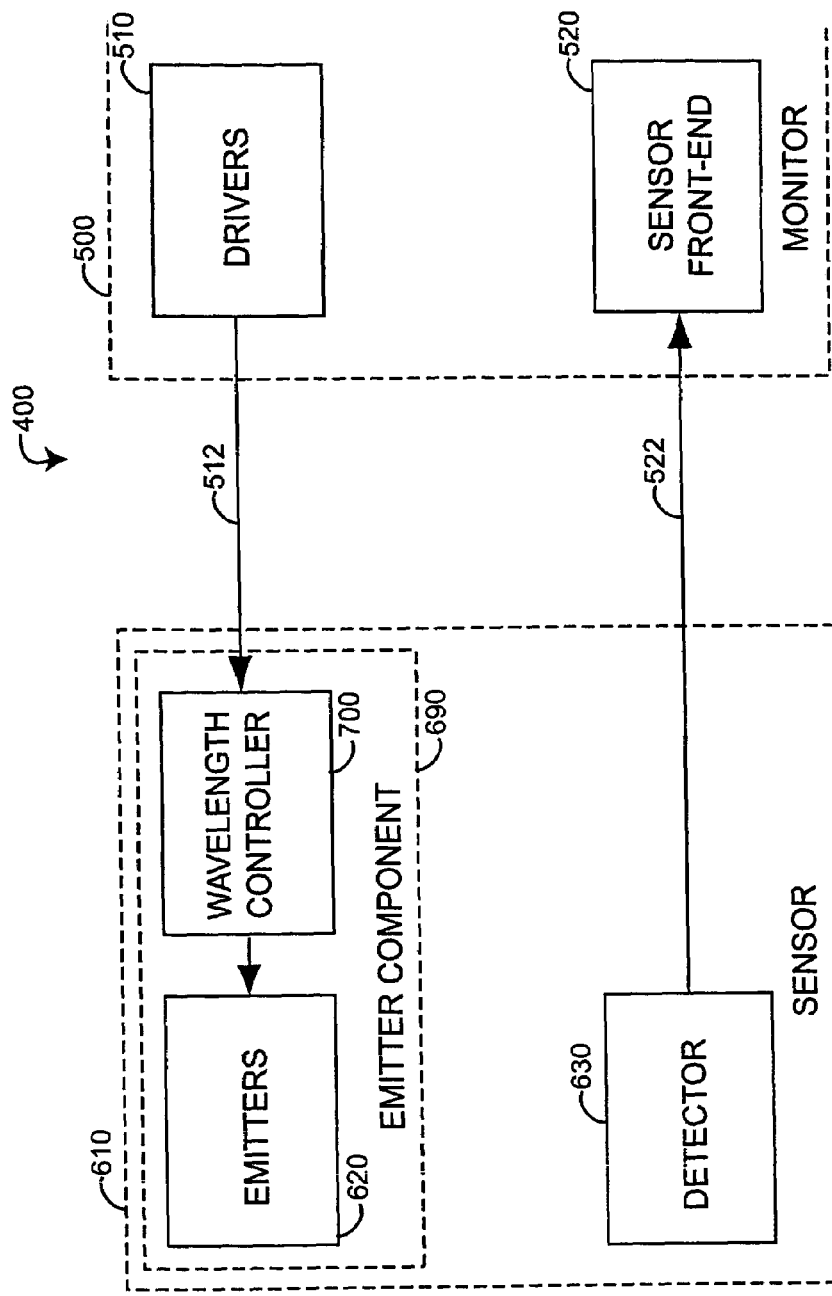

FIGS. 6A–C illustrate various embodiments of a blood parameter measurement system 400 utilizing an upgraded pulse oximetry monitor 500. FIG. 6A illustrates a monitor 500 connected to an adaptive multiple wavelength sensor 610. The sensor 610 has emitters 620, at least one detector 630 and a wavelength controller 700. The emitters 620 are capable of illuminating a tissue site with multiple wavelengths. The detector 630 receives multiple wavelengths after transmission through or reflection from the tissue site and provides a corresponding modulated sensor signal output 522. The wavelength controller 700 advantageously interfaces to a conventional driver 510 configured to provide a drive signal output 512 to red and IR LEDs 210, 220 (FIGS. 2A–C), as described above. The driver 510 generates an encoded drive signal 512 according to the sampling software modification 560 (FIG. 5), described above. The wavelength controller 700 decodes the drive signal 512 and enables the emitters 620 accordingly, as described in further detail with respect to FIGS. 7–11, below.

FIG. 6B illustrates a monitor 500 connected to an adapter cable 650. Advantageously, the adapter cable 650 functions as an interface between an upgraded monitor 500 and an otherwise incompatible multiple wavelength sensor 660. The adapter cable 650 has a wavelength controller 700 that functions in a manner similar to that described with respect to FIG. 6A, above. In particular, the wavelength controller 700 decodes the drive signal 512 and provides corresponding multiple emitter drive signals 652 to the sensor emitters 660.

FIG. 6C illustrates a monitor 500 connected to an adaptive multiple wavelength sensor 610 incorporating a multiple emitter component 690. In one embodiment, the emitter component 690 has multiple emitters 620 and a wavelength controller 700 mounted on an encapsulated carrier. Advantageously, the emitter component 690 may be configured to substitute for or replace a dual LED component within a conventional pulse oximeter sensor so as to convert a pulse oximeter sensor into an adaptive multiple wavelength sensor without the tooling and manufacturing overhead of a unique sensor assembly. In a particularly advantageous embodiment, the wavelength controller 700 is configured such that the adaptive multiple wavelength sensor 610 is backward compatible with monitors that do not have the blood parameter upgrade 410. For example, if the wavelength controller 700 is unable to detect an upgrade encoded pattern in the drive signal 512, the wavelength controller 700 defaults to routing the drive signal 512 to a pair of LEDs having conventional wavelengths and a conventional configuration, as described with respect to FIGS. 2A–C, above. In this manner, a common sensor could be used for either conventional two wavelength pulse oximetry or for expanded multiple wavelength blood parameter measurement capability.

The sensors 610, 660 described with respect to FIGS. 6A–C, above, may have multiple detectors 630 that are enabled by the wavelength controller 700 in conjunction with particular emitters or groups of emitters 620. In this manner, the effective detector bandwidth may be advantageously increased to accommodate the emitter wavelengths. Multiple detector sensor circuits are described with respect to FIGS. 10A–B, below.

Figure 7:
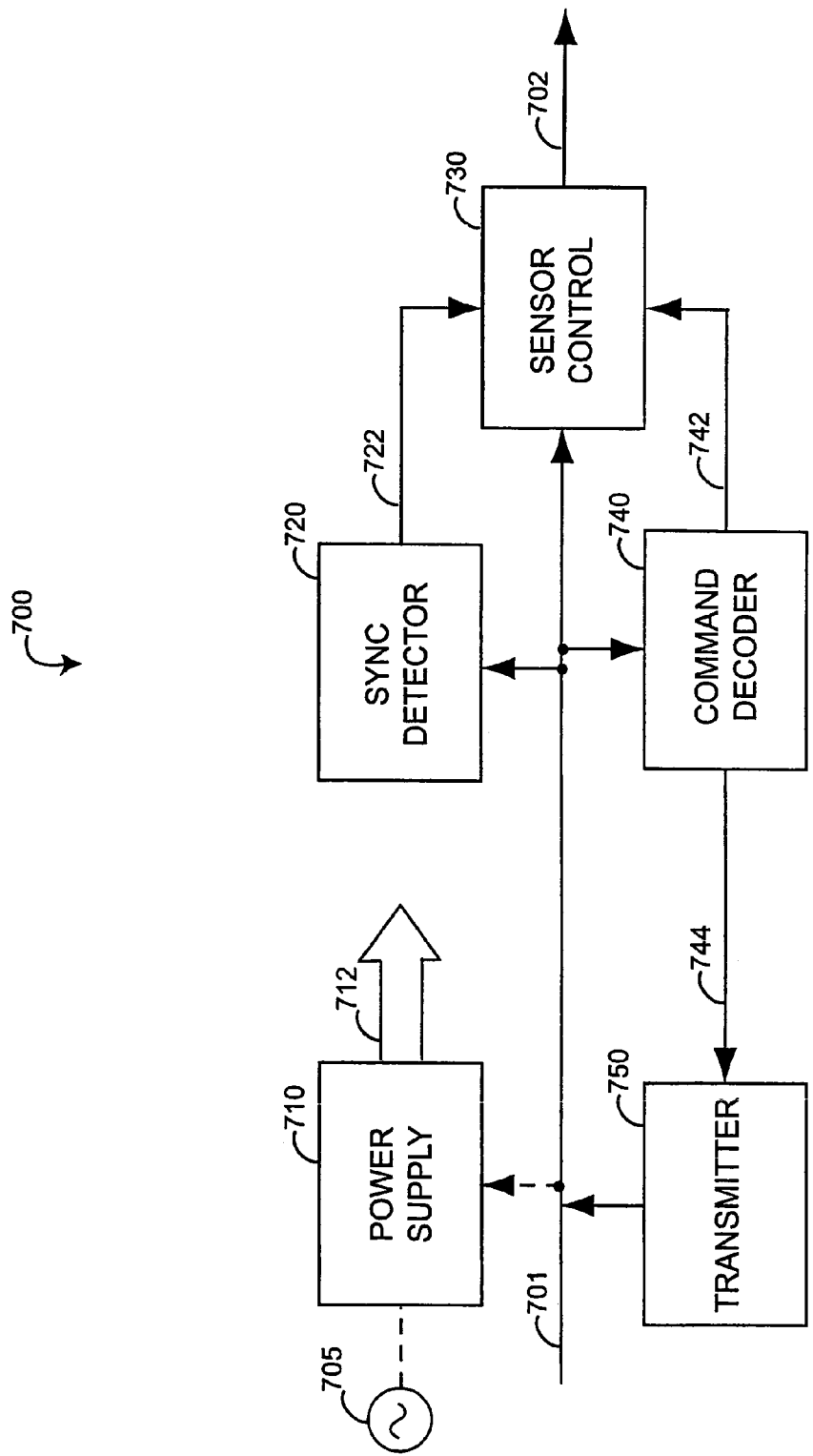
FIG. 7 is a top-level block diagram of a wavelength controller.

FIG. 7 illustrates a wavelength controller 700 having a drive signal input 701, a power supply 710, a sync detector 720, a sensor control 730 and sensor control output 702. The drive signal input 701 is configured to receive the monitor drive signal 512 (FIG. 5). The power supply 710 supplies DC power 712 to the remainder of the wavelength controller 700 and may derive power from any number of input sources, such as a battery, an external AC or DC supply 705, or the drive signal input 701. The sync detector 720 decodes the drive signal input 701 to determine the occurrence of a sync pattern in the drive signal waveform and provides a sync output 722 that indicates a sync event to the sensor control 730 accordingly. A sync pattern may be encoded as a unique pulse pattern on the drive signal 512 (FIG. 5) by the sampling software modification 560 (FIG. 5). The sensor control 730 utilizes the sync output 722 to synchronize emitter selection with the upgrade software 410 (FIG. 4), so that the upgrade software 410 (FIG. 4) can properly identify and process detector response at each wavelength, as described below. The sensor control 730 is responsive to drive current pulses on the drive signal input 701 so as to sequentially select particular sensor emitters 620 (FIGS. 6A–C). The sensor control output 702 routes the drive signal 512 (FIG. 5) from the drive signal input 701 to the selected emitters 620 (FIGS. 6A–C).

As shown in FIG. 7, the wavelength controller 700 may also have a command decoder 740 and a transmitter 750. The command decoder 740 determines the occurrence of a command pattern in the drive signal waveform and provides a command output 742, 744 to the sensor control 730 and/or the transmitter 744 in response. Commands may be encoded as one or more unique pulse patterns on the drive signal 512 (FIG. 5) by the sampling software modification 560 (FIG. 5). A command, for example, may program the sensor control 730 for a particular emitter enabling sequence or instruct the transmitter 750 to send. The transmitter 750 is configured to send sensor status or other sensor information to the monitor 500 (FIG. 5) when the drive signal 512 (FIG. 5) is off. To receive such information, the monitor 500 (FIG. 5) would have a corresponding receiver (not shown) sharing the drive conductors as inputs.

Figure 8A:
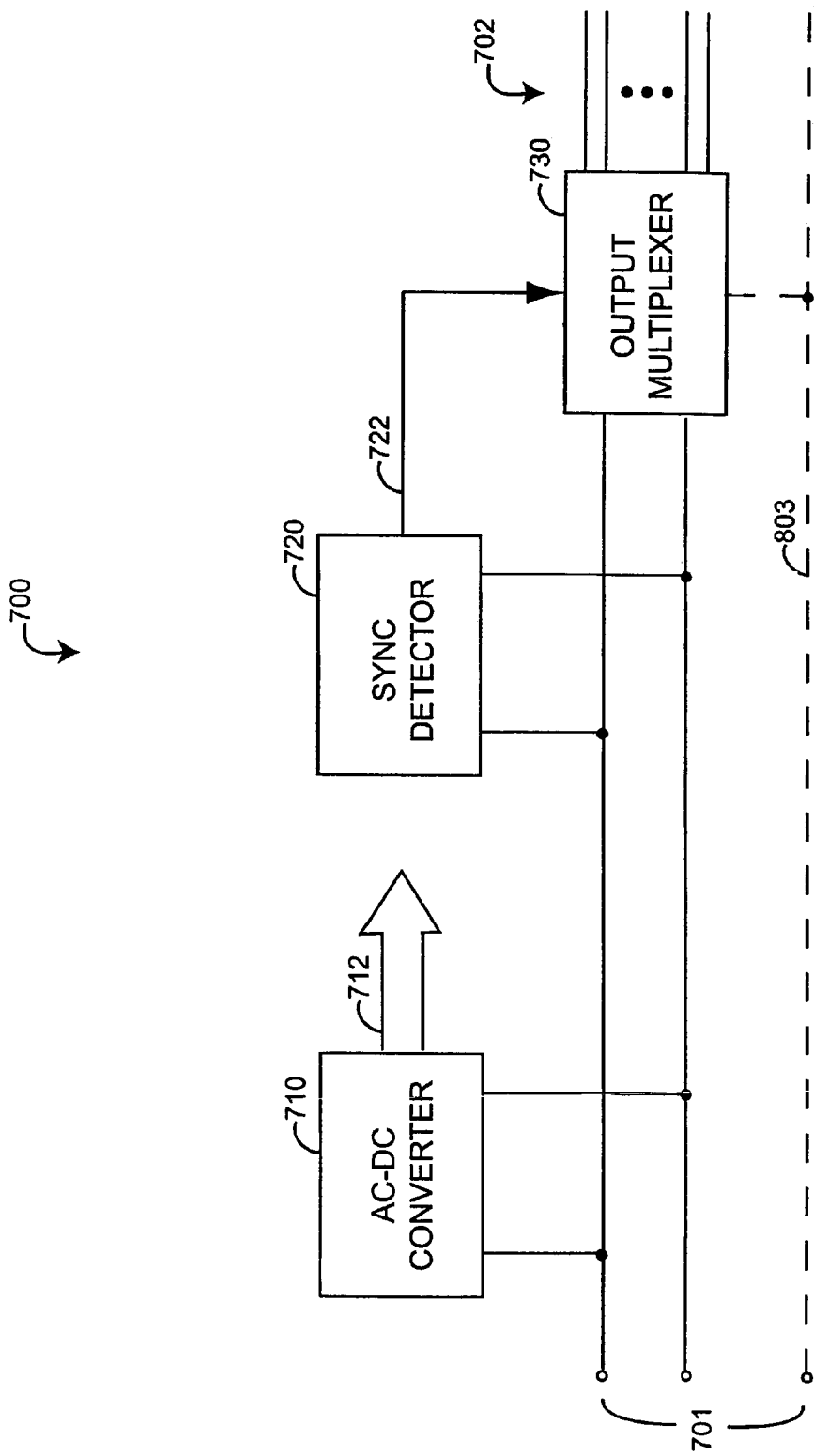
FIGS. 8A–B are detailed block diagrams of a wavelength controller embodiment and a wavelength control element embodiment of a wavelength controller portion, respectively.

FIG. 8A illustrates one wavelength controller 700 embodiment having a drive signal input 701, an AC–DC converter 710, a sync detector 720, an output multiplexer 740 and sensor control outputs 702. A drive signal 512 (FIG. 5) is provided on the drive control input 701, as described with respect to FIG. 7, above. The drive signal input 701 may have, for example, two conductors to accommodate a bipolar drive signal, such as described with respect to FIG. 3B, above, or it may have an additional common conductor 803 to accommodate two unipolar drive signals, such as described with respect to FIG. 3C, above. The converter 710 pulls some current from the drive signal input 701 so as to provide DC power 712 to the controller electronics. The sync detector 720 decodes the drive signal input 701 and provides a sync output 722, as described with respect to FIG. 7, above The output multiplexer 730 routes the drive signal input 701 to a selected pair of sensor control outputs 702. Each pair of sensor control outputs 702 is in communication with a pair of emitters 620 (FIGS. 6A–C), such as described with respect to FIGS. 9A–B, below.

In operation, the sync output 722 initializes the output multiplexer 740 so that a first pair of sensor control outputs 702 is selected, which selects a predetermined pair of emitters 620 (FIGS. 6A–C). Individual ones of a selected emitter pair are then enabled according to the drive current waveform, as described with respect to FIGS. 3A–C, above. The drive current waveform on the drive signal input 701 also causes the output multiplexer 740 to enable other pairs of drive outputs 702, selecting other emitter pairs in a predetermined sequence.

Figure 8B:
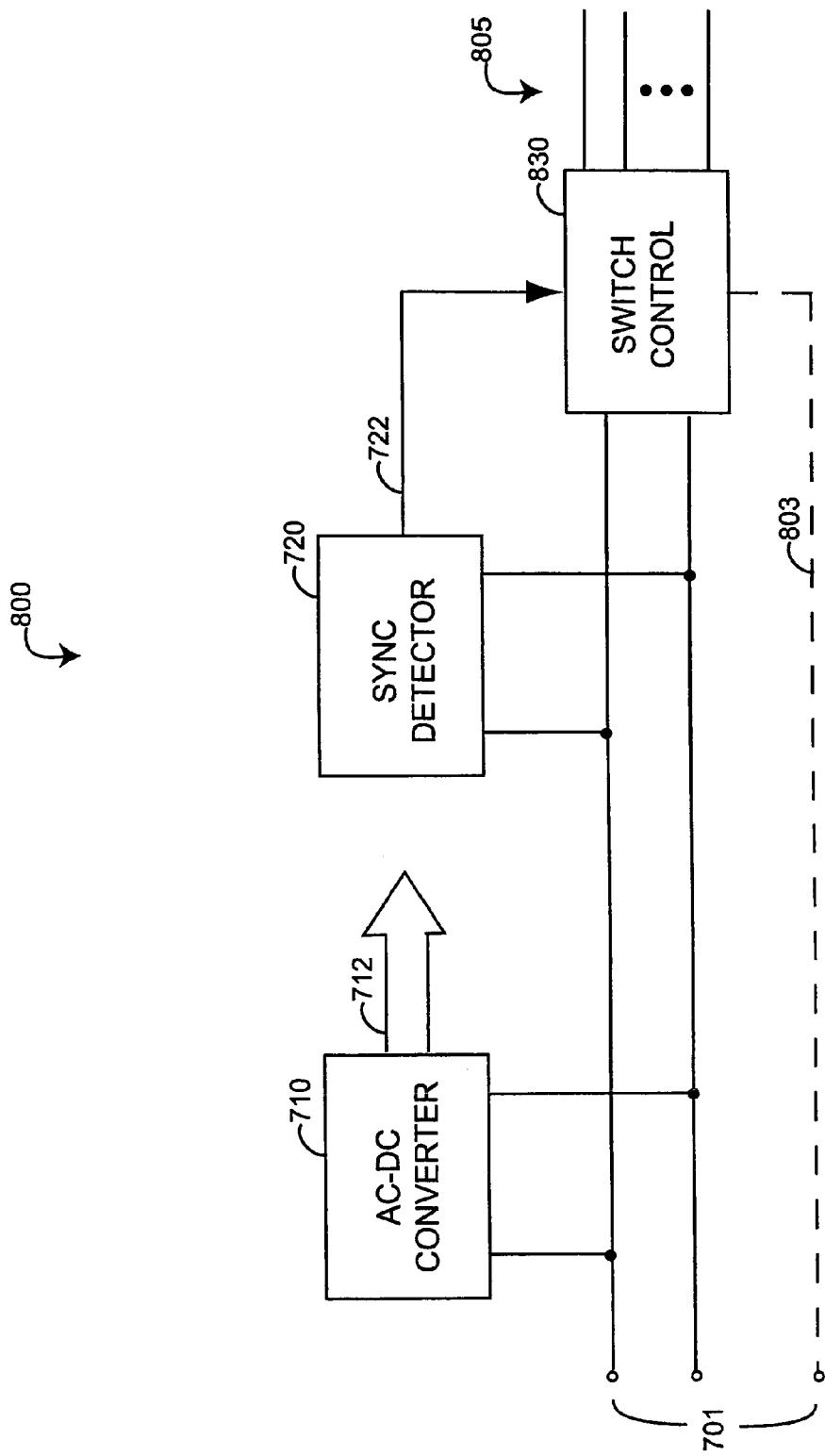

FIG. 8B illustrates a wavelength control element 800 that functions in combination with switches 1010 (FIGS. 10A–B) as a wavelength controller 700 (FIG. 7) embodiment, as described above. The wavelength control element 800 has an input 701, an AC–DC converter 710 and a sync detector 930 that function as described with respect to FIG. 8A, above. The wavelength control element 800 also has a switch control 830 that functions in combination with switches 1010 (FIGS. 10A–B) to route the drive signal input 701 to selected pairs of emitters 620 (FIGS. 6A–C), such as described with respect to FIGS. 10A–B, below. In particular, each switch control output 805 actuates one or more switches to connect or disconnect a selected emitter pair to the drive signal 512 (FIG. 5).

In operation, the sync output 722 initializes the switch control 830 so that a first switch control output 805 is selected, which actuates a switch or switches that connect a predetermined pair of emitters 620 (FIGS. 6A–C) to the drive signal 512 (FIG. 5). Individual ones of a selected emitter pair are then enabled according to the drive current waveform, as described with respect to FIGS. 3A–C, above.

The drive current waveform on the drive signal input 701 also causes the switch control 830 to enable other switch control outputs 805, selecting other emitter pairs in a predetermined sequence.

Figure 9A:
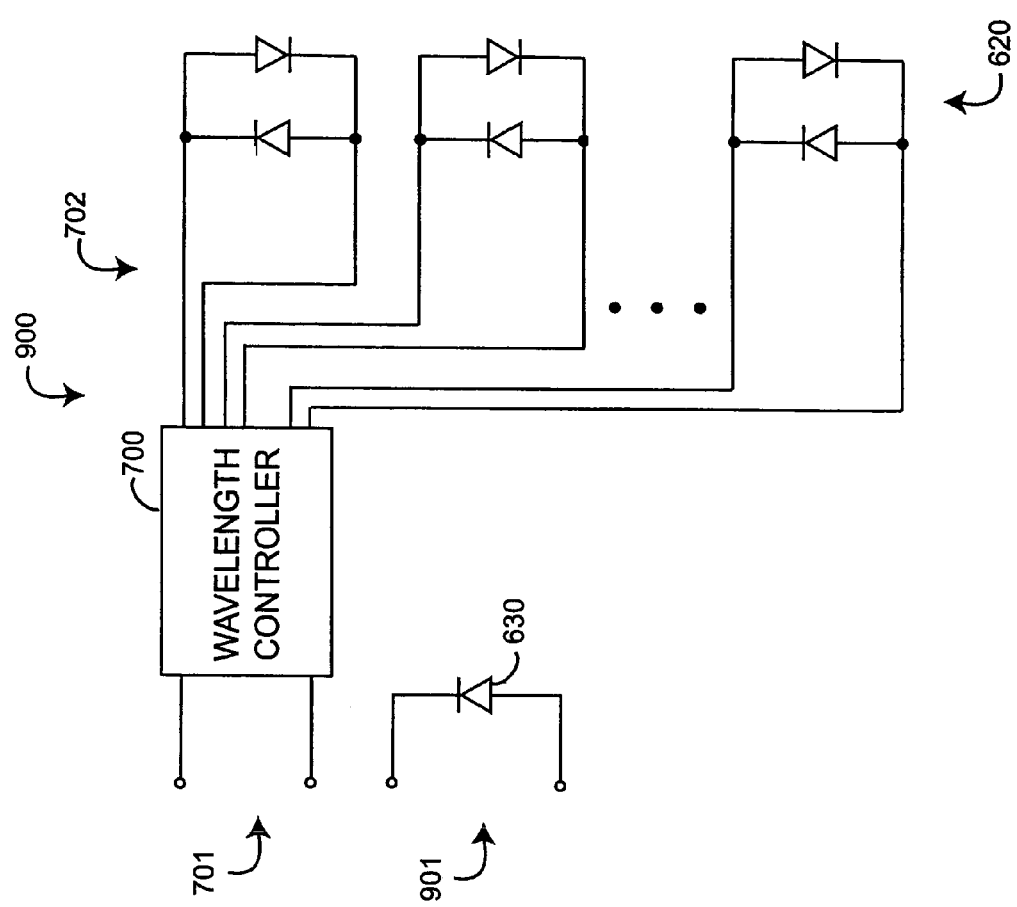
FIGS. 9A–B are schematic diagrams of a multiple wavelength sensor incorporating a wavelength controller.
Figure 9B:
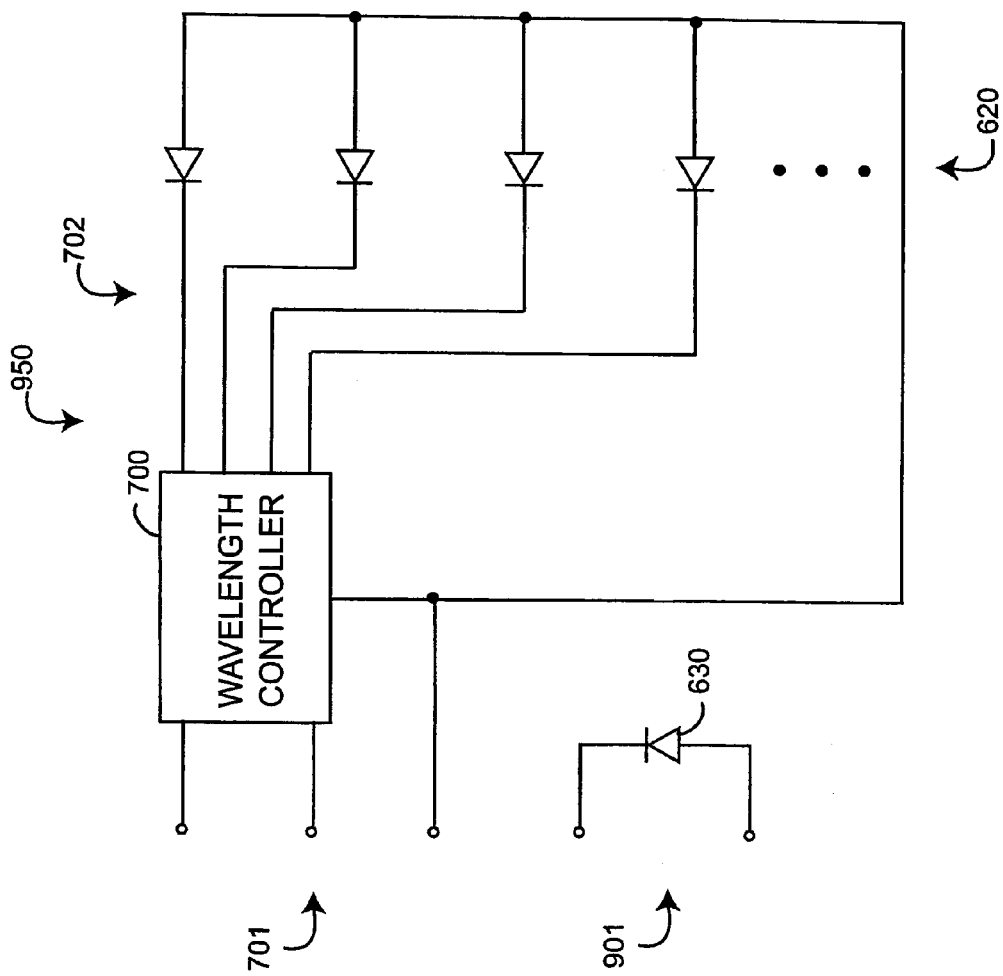

FIGS. 9A–B illustrate back-to-back LED and common anode LED embodiments of a sensor circuit 900, 950 respectively, each having LEDs 620, a photodiode 630 and a wavelength controller 700. The drive signal inputs 701 connect to the drivers 510 (FIG. 5) so as to receive a drive signal 512 (FIG. 5). Photodiode pinouts 901 connect to the sensor front-end 520 (FIG. 5) so as to provide a detector signal 522 (FIG. 5). The wavelength controller 700 selects a pair of LEDs 620 in response to the drive signal 512 (FIG. 5) on the drive signal input 701, communicating the drive signal 512 (FIG. 5) to the selected LEDs 620. These elements may be incorporated into an adaptive sensor 610 (FIGS. 6A, C) or in a combination adapter cable 650 (FIG. 6B) and multiple wavelength sensor 660 (FIG. 6B). With respect to FIG. 9A, a bipolar drive current, having characteristics similar to those described with respect to FIG. 3B, above, enables individual LEDs of a selected back-to-back LED pair. With respect to FIG. 9B, a pair of unipolar drive currents, having characteristics similar to those described with respect to FIG. 3C, above, enables individual LEDs of a selected common anode LED pair. A similar sensor circuit would accommodate common cathode LEDs. The sequence and timing of LED selection is described in detail with respect to FIGS. 11A–B, below.

Figure 10A:
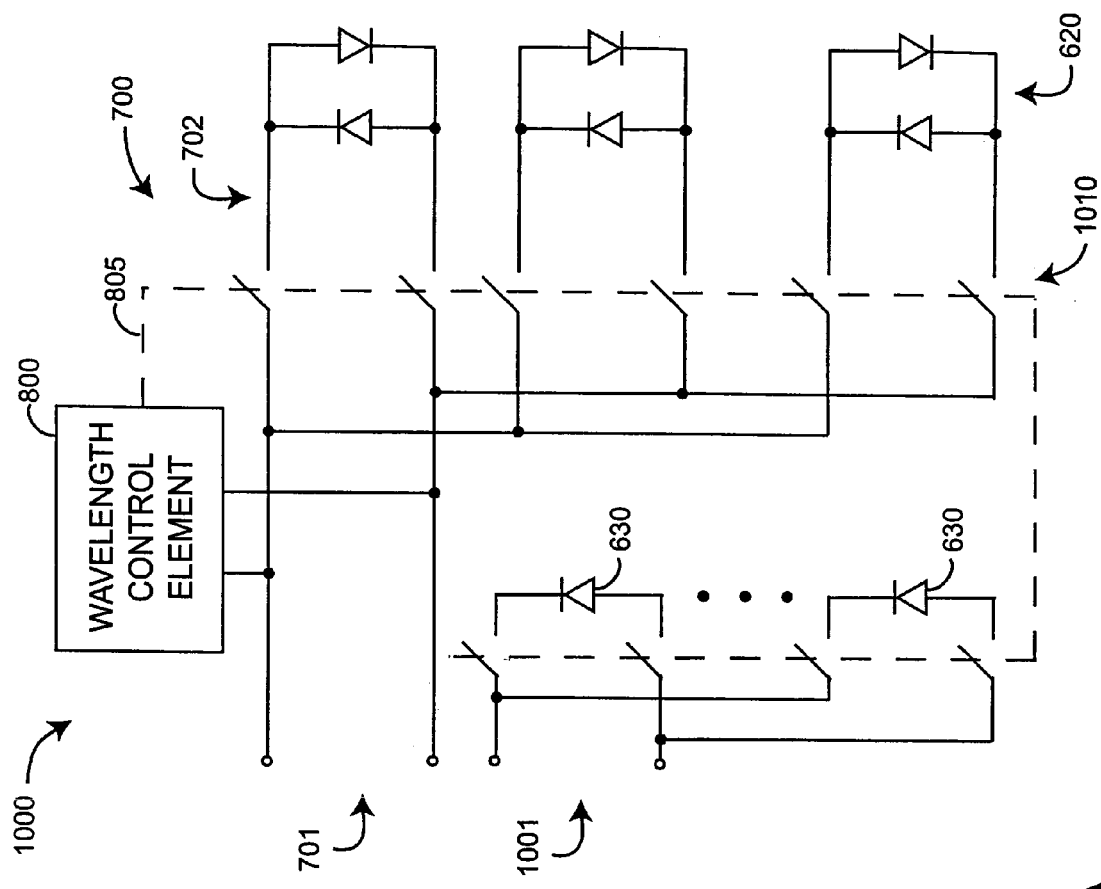
FIGS. 10A–B are schematic diagrams of a multiple wavelength sensor incorporating a wavelength control element and corresponding switches.
Figure 10B:
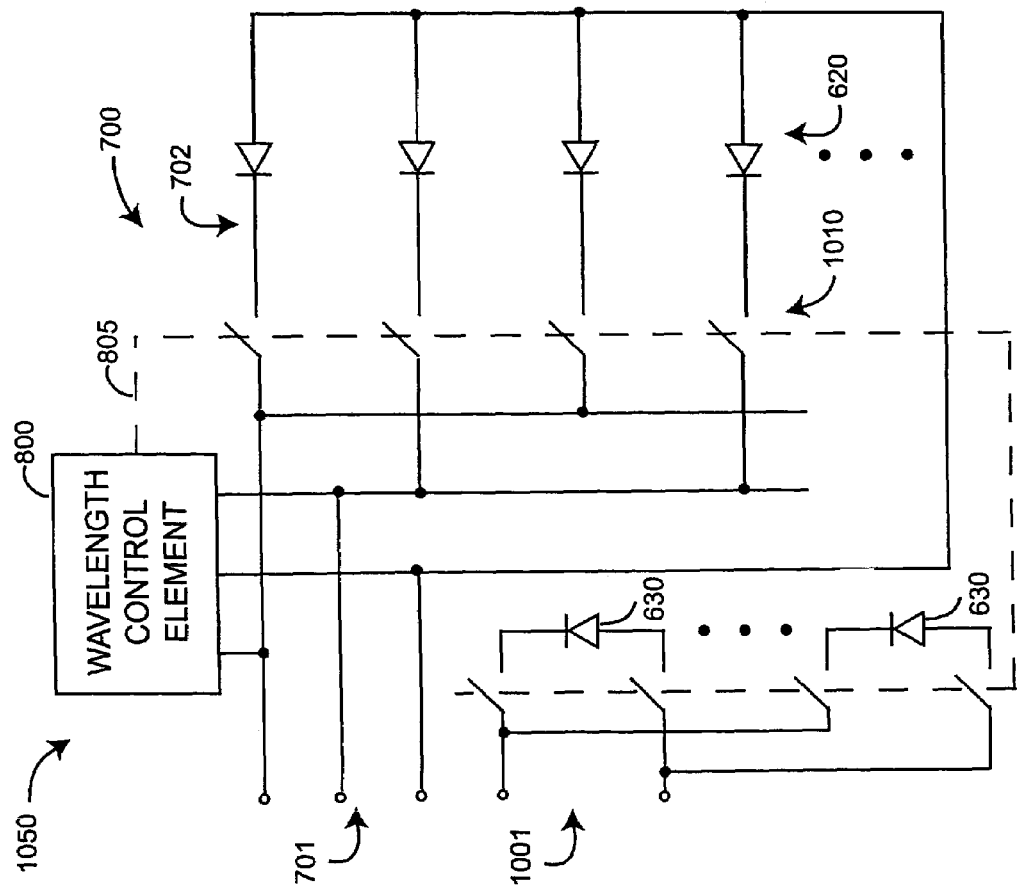

FIGS. 10A–B illustrate back-to-back LED and common anode LED embodiments of a sensor circuit 1000, 1050, respectively, each having LEDs 620, photodiodes 630 and a wavelength control element 800. A drive signal input 701 connects to the drivers 510 (FIG. 5) so as to receive a drive signal 512 (FIG. 5). Photodiode pinouts 1001 connect to the sensor front-end 520 (FIG. 5) so as to provide a detector signal 522 (FIG. 5). The wavelength control element 800 selects a pair of LEDs 620 in response to the drive signal 512 (FIG. 5) on the drive signal input 701. Each LED pair is selectable by the switches 1010, which either connect an LED pair to the drive signal input 701 or isolate an LED pair from the drive signal input 701. In a multiple photodiode embodiment, the wavelength control element 800 also selects a corresponding photodiode 630. Each photodiode 630 is selectable by the switches 1010, which either connect it to, or isolate it from, the photodiode pinouts 1001. Multiple photodiodes 630 advantageously allow optical radiation detection over a broader range of wavelengths than practical from a single photodiode, due to the bandwidth limitations of such components. The switches 1010 are actuated so as to select a photodiode 630 having an operating range that corresponds to the wavelength of the selected LEDs 620.

These elements may be incorporated into an adaptive sensor 610 (FIGS. 6A, C) or in a combination adapter cable 650 (FIG. 6B) and multiple wavelength sensor 660 (FIG. 6B). With respect to FIG. 10A, a bipolar drive current, having characteristics similar to those described with respect to FIG. 3B, above, enables individual LEDs of a selected back-to-back pair. With respect to FIG. 10B, a pair of unipolar drive currents, having characteristics similar to those described with respect to FIG. 3C, above, enables individual LEDs of a selected common anode pair. A similar sensor circuit would accommodate common cathode LEDs. The switches 1010 may be electromechanical or electronic devices, such as field-effect transistors (FETs). The sequence and timing of LED selection is described in detail with respect to FIGS. 11A–B, below.

Figure 11A:
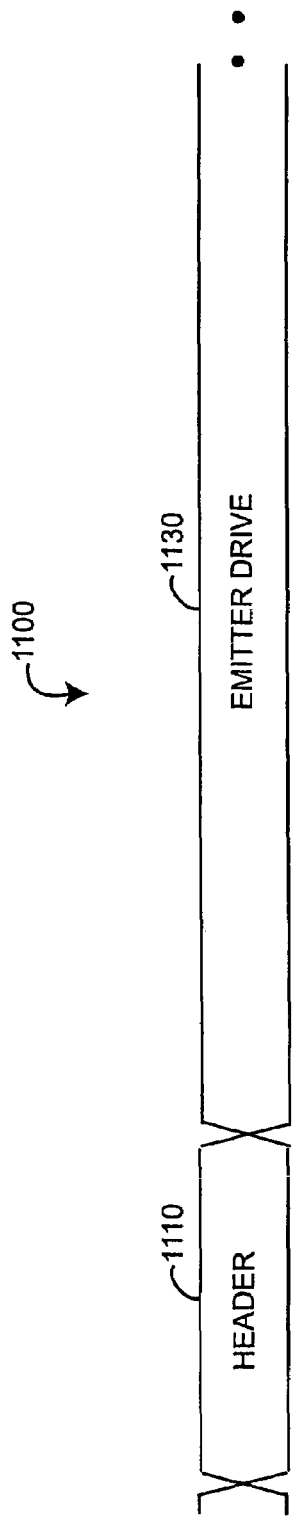
FIGS. 11A–B are multiple-wavelength timing diagrams.
Figure 11B:
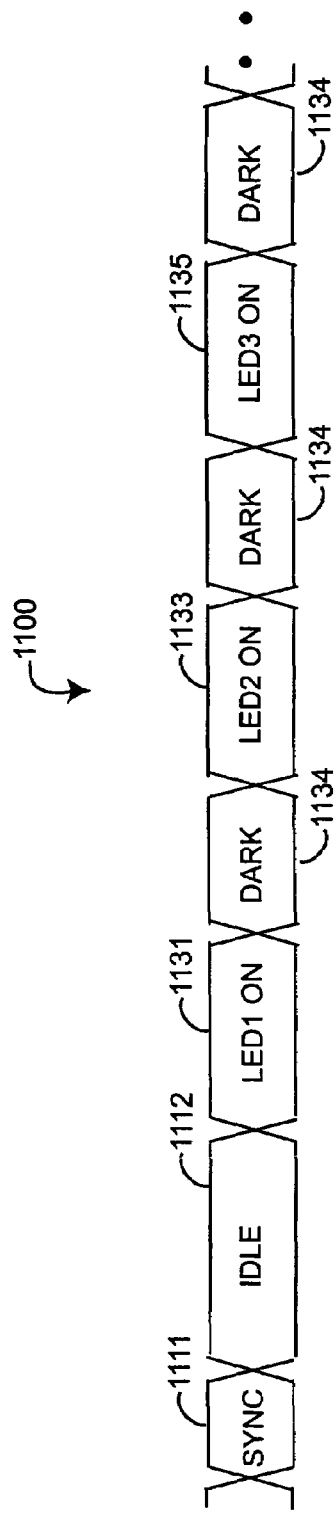

FIGS. 11A–B illustrate multiple wavelength control timing, as generated by a sampling controller 550 (FIG. 5), according to a sampling software upgrade 560 (FIG. 5). As shown in FIG. 11A, the control timing 1100 includes a header interval 1110 and an emitter drive interval 1130. The header 1110 may include one or more of sync, command, transmission and idle time periods. During a sync time period, an encoded drive waveform is generated for the sync detector 720 (FIG. 7), as described above. During a command time period, an encoded drive waveform is generated for the command decoder 740 (FIG. 7), as described above. During the transmission time period, the drivers 510 (FIG. 5) have a high impedance output, for example, so that the transmitter 750 (FIG. 7) may send on the same conductors as the drive signal 512 (FIG. 5), as described above. The drive interval 1130 may include multiple drive current pulses and interleaved dark periods, as described with respect to FIGS. 3A–C, above.

As shown in FIG. 11B, one embodiment of the control timing 1100 includes a sync period 1111 and an idle period 1112 in the header interval 1110 and a sequence of LED enable periods 1131–1135 interleaved with dark periods 1134 during the emitter drive interval 1130. During the sync period 1110 the sampling controller 550 (FIG. 5) and signal processor 530 (FIG. 5) in the monitor are synchronized with the wavelength controller in the sensor. In this manner, the signal processor can determine which wavelength response corresponds to the detector signal 522 (FIG. 5) at any particular time. During the LED enable periods 1131–1135, the drivers 510 (FIG. 5) generate drive current that is routed by the wavelength controller to the LEDs in a predetermined sequence, as described with respect to FIGS. 7–10, above.

The LED enable sequence 1131, 1133, 1135 can be any number of patterns. For example, for a three-wavelength sensor, the LED enable pattern can be 1, 2, 3, 1, 2, 3, . . . as shown, where the numbers correspond to individual LEDs, such as an IR LED and two red LEDs. As another example, the LED enable pattern can be 1, 2, 1, 3, 1, 2, 1, 3, . . . Further, the duration or duty cycle of LED enable periods can vary. For example, for a three-wavelength sensor, the duration for each LED enable period and each dark period can be the same, such that each LED has a 16.7% duty cycle. As another example, the IR LED can have a 28.6% duty cycle and the red LEDs can each have a 14.3% duty cycle, to name just a few timing variations.

A blood parameter measurement system has been disclosed in detail in connection with various embodiments. These embodiments are disclosed by way of examples only and are not to limit the scope of the claims that follow. One of ordinary skill in the art will appreciate many variations and modifications.

What is claimed is:

1. A blood parameter measurement system comprising:
    a monitor configured to provide an oxygen saturation measurement based upon the absorption of two wavelengths of optical radiation by a tissue site;
    a software upgrade installable in said monitor so as to enable said monitor to operate in conjunction with a multiple wavelength sensor; and
    a wavelength controller adapted to said upgrade so as to drive said sensor, wherein said upgrade comprises:
        sampling software providing a drive waveform for said sensor; and
        signal processing software adapted to demodulate a multiplexed signal from said sensor.

2. The blood parameter measurement system according to claim 1 wherein said drive waveform comprises:
    a header interval that controls said wavelength controller; and
    an emitter drive interval that enables drive current to said sensor.

3. The blood parameter measurement system according to claim 2 wherein said header interval comprises a sync period decodable by said wavelength controller so as to synchronize said wavelength controller and said upgrade.

4. The blood parameter measurement system according to claim 2 wherein said header interval comprises a command interval decodable by said wavelength controller so as to allow said upgrade to command said wavelength controller.

5. A blood parameter measurement system comprising:
    a monitor configured to provide an oxygen saturation measurement based upon the absorption of two wavelengths of optical radiation by a tissue site;
    a software upgrade installable in said monitor so as to enable said monitor to operate in conjunction with a multiple wavelength sensor; and
    a wavelength controller adapted to said upgrade so as to drive said sensor, wherein said wavelength controller is located in an adapter cable, and said adapter cable provides an interface between the sensor port of said monitor and said sensor.

6. A blood parameter measurement system comprising:
    a monitor configured to provide an oxygen saturation measurement based upon the absorption of two wavelengths of optical radiation by a tissue site;
    a software upgrade installable in said monitor so as to enable said monitor to operate in conjunction with a multiple wavelength sensor; and
    a wavelength controller adapted to said upgrade so as to drive said sensor, wherein said wavelength controller is integrated into said sensor.

7. The blood parameter measurement system according to claim 6 wherein said wavelength controller is co-located with multiple LEDs within an emitter component, said emitter component adapted to substitute for a two-wavelength emitter component within a pulse oximetry sensor.

8. A blood parameter measurement system comprising:
    a monitor configured to provide an oxygen saturation measurement based upon the absorption of two wavelengths of optical radiation by a tissue site;
    a software upgrade installable in said monitor so as to enable said monitor to operate in conjunction with a multiple wavelength sensor; and
    a wavelength controller adapted to said upgrade so as to drive said sensor, wherein said wavelength controller comprises:
        a sensor control configured to route a drive signal to a select one of a plurality of sensor emitters; and
        a sync detector adapted to decode a sync interval on said drive signal so as to synchronize the operations of said software upgrade and said wavelength controller.

9. The blood parameter measurement system according to claim 8 wherein said wavelength controller further comprises a command decoder adapted to decode a command interval on said drive signal so as to accept commands from said software upgrade.

10. The blood parameter measurement system according to claim 8 wherein said wavelength controller further comprises a transmitter configured to communicate sensor information to said monitor on conductors that communicate said drive signal.

11. The blood parameter measurement system according to claim 8 wherein said sensor control comprises an output multiplexer that routes said drive signal to selected emitters of said sensor.

12. The blood parameter measurement system according to claim 8 wherein said sensor control comprises:
a plurality of switches configured to connect and disconnect said drive signal and emitters of said sensor; and
a switch control configured to actuate select ones of said switches.

13. A blood parameter measurement method comprising the steps of:
communicating a drive, signal from a monitor to a sensor;
synchronizing said sensor with said monitor;
sequentially enabling a plurality of emitters of said sensor; and
communicating a sensor signal from said sensor to said monitor, wherein said synchronizing step comprises the substeps of:
inputting said drive signal to a wavelength controller; and
decoding a header interval of said drive signal so as to detect a sync event.

14. The blood parameter measurement method according to claim 13 wherein said enabling step comprises the substeps of:
selecting a predetermined first emitter pair of said sensor in response to said sync event;
routing said drive signal to said first emitter pair, and activating said first emitter pair during a drive interval of said drive signal.

15. The blood parameter measurement method according to claim 14 wherein said enabling step comprises the further substeps of:
deactivating said first emitter pair;
selecting a predetermined second emitter pair to follow said first emitter pair;
routing said drive signal to said second emitter pair and activating said second emitter pair during a drive interval of said drive signal.

16. A blood parameter measurement system comprising:
a multiple wavelength sensor means for illuminating a tissue site with at least three wavelengths and detecting a corresponding tissue sfte response;
a software upgrade means for enabling a pulse oximetry monitor to drive said sensor and process a corresponding sensor signal; and
a wavelength controller means for interfacing between said software upgrade means and said multiple wavelength sensor means.

17. The blood parameter measurement system according to claim 16 wherein said software upgrade means comprises:
a sampling controller means for generating an encoded drive signal; and
a signal processing means for demodulating said sensor signal.

18. The blood parameter measurement system according to claim 17 wherein said wavelength controller means comprises a sync decoder means for synchronizing with said software upgrade means in response to said encoded drive signal.

19. The blood parameter measurement system according to claim 16 wherein said wavelength controller means comprises a sensor control means for routing a drive signal from said monitor to a selected one of a plurality of sensor emitters.

* * * * *

UNITED STATES PATENT AND TRADEMARK OFFICE
CERTIFICATE OF CORRECTION

PATENT NO. : 7,027,849 B2 Page 1 of 1
APPLICATION NO. : 10/719928
DATED : April 11, 2006
INVENTOR(S) : Al-Ali It is certified that error appears in the above-identified patent and that said Letters Patent is hereby corrected as shown below:

On Title Page

Page 2, column 2 (U.S. Patent Documents), line 14, after "6,658,276" delete "B1" and insert -- B2 --, therefore.

Sheet 3 of 16 (Fig. 3A), Rigtht hand side (Beside Box 330), delete " C " and insert -- C⋅ --, therefore.

Column 3, line 12, delete "$\epsilon_{i,\lambda}$" and insert --$\varepsilon_{i,\lambda}$--, therefore.

Column 8, line 64, delete "electromechanical" and inset -- electro-mechanical --, therefore.

Column 9, line 43, delete "dutv" and insert -- duty --, therefore.

Column 11, line 13, in Claim 13, delete "drive," and insert -- drive --, therefore.

Column 11, line 29, in Claim 14, delete "pair," and insert -- pair; --, therefore.

Column 12, line 4, in Claim 15, after "pair" insert -- ; --.

Column 12, line 10, in Claim 16, delete "sfte" and insert -- site --, therefore.

Signed and Sealed this

Tenth Day of July, 2007

JON W. DUDAS
*Director of the United States Patent and Trademark Office*